United States Patent [19]

Vallerien

[11] Patent Number: 5,426,202

[45] Date of Patent: Jun. 20, 1995

[54] ALKYL TIN COMPOUNDS, THEIR SYNTHESIS AND ELECTRICALLY CONDUCTIVE AND IR-REFLECTING LAYERS

[75] Inventor: Sven-Uwe Vallerien, Essen, Germany

[73] Assignee: Th. Goldschmidt AG, Essen, Germany

[21] Appl. No.: 272,369

[22] Filed: Jul. 8, 1994

[30] Foreign Application Priority Data

Jul. 30, 1993 [DE] Germany .................. 43 25 648.1

[51] Int. Cl.$^6$ ................................. C07F 7/22
[52] U.S. Cl. ........................ 556/90; 556/94; 556/105; 252/518
[58] Field of Search ............... 556/90, 94, 105

[56] References Cited

U.S. PATENT DOCUMENTS

| | | | |
|---|---|---|---|
| 3,562,305 | 2/1971 | Hoch | 260/429.7 |
| 3,759,743 | 9/1973 | Menke | 117/211 |
| 4,731,462 | 3/1988 | Russo et al. | 556/105 |

*Primary Examiner*—José G. Dees
*Assistant Examiner*—Porfirio Nazario-Gonzalez
*Attorney, Agent, or Firm*—Anderson Kill Olick & Oshinsky

[57] ABSTRACT

The invention relates to compounds of the general formula $SnR^1{}_aR^2{}_bR^3{}_c$, in which $R^1$ is an alkyl group with 1 to 4 carbon atoms, $R^2$ is an acetate group, $R^3$ is a trifluoroacetate group, a has a value of 1 or 2, b has a value of 1 or 2 and c has a value of 1 or 2, with the proviso that the sum of $a+b+c=4$. The invention also relates to a method for the synthesis of these compounds and to a material for producing electrically conductive and infrared-reflective fluorine-doped tin oxide layers on glass, glass ceramic and/or enamel surfaces, the material containing tin compounds of the formula $SnR^1{}_aR^2{}_bR^3{}_c$ or mixtures of these tin compounds, the mixture corresponding to the general formula $SnR^1{}_xR^2{}_yR^3{}_z$, wherein x has a numerical value of 1 to 2, y a numerical value of 0.1 to 2.9 and z a numerical value of 0.1 to 2.9, the sum of $x+y+z$ being 4, dissolved in a polar organic solvent.

6 Claims, No Drawings

ALKYL TIN COMPOUNDS, THEIR SYNTHESIS AND ELECTRICALLY CONDUCTIVE AND IR-REFLECTING LAYERS

FIELD OF INVENTION

The invention relates to new alkyl tin compounds with acetate and trifluoroacetate groups, as well to as their synthesis. The invention furthermore relates to materials containing these new tin compounds for the formation of electrically conductive and infrared-reflecting layers on surfaces of glass, glass ceramic or enamel.

BACKGROUND INFORMATION AND PRIOR ART

It is well known that electrically conductive, fluorine-doped tin oxide layers on glass surfaces decrease the electrical resistance of the coated surfaces as well as increase the infrared reflection. To produce such layers, suitable tin compounds (basic compounds) are brought simultaneously with a fluorine-emitting compound (doping agent) into contact with the glass surface, which has been heated to a temperature of 400° to 800° C. The basic tin compound forms a coherent tin oxide layer on the surface of the glass, the glass ceramic or the enamel. The fluorine from the doping agent increases the electrical conductivity and brings about the high infrared reflection.

Spraying suitable tin-containing and fluorine-containing solutions for applying the fluorine-doped tin oxide layers on the surfaces is technologically very simple.

In the German Offenlegungsschrift 22 46 193, a method is disclosed for preparing transparent, electrically conductive tin oxide films on glass surfaces. For this method, the solution of an organo-tin salt of trifluoroacetic acid in methyl ethyl ketone is used. To prepare the solutions, several expensive steps are required. The tin carboxylates, produced by this method, have a fluorine content, which is too high but specified by the molecular structure. However, excessive doping with fluorine leads to a distinct deterioration in the infrared reflection and the electrical conductivity.

In the German Offenlegungsschrift 39 15 232, a method is disclosed for preparing electrically conductive, IR-reflecting, fluorine-doped tin oxide layers by applying an organic solution of reaction products of trifluoroacetic acid and alkyl tin oxides on the surface heated to a temperature of 400° to 700° C. Ethyl acetate and/or methyl ethyl ketone are used as solvents here. The resulting addition products are, however, not stable. The desirable use of polar, lower alcohols, such as ethanol or isopropanol, as solvents, which, as is well known to those skilled in the art, leads to optically defect-free, uniform layers, is not possible with these compounds.

In the European publication 0 318 486, chloro-tin acetate trifluoroacetates are disclosed. These compounds are synthesized by a multi-step expensive method. The function values of a tin oxide layer, 200 nm thick, produced with these compounds, are of the order of 70% IR-reflection and an electric surface resistance of 40 ohms/square. The main disadvantage of these substances, is however, the presence of chlorine. One of the substances formed during pyrolysis is hydrogen chloride gas, which attacks or damages materials and can endanger health.

OBJECT OF THE INVENTION

An object of the present invention is novel alkyl tin compounds. Another object of the invention is a method for synthesizing inventive compounds. Yet another object of the present invention is the material containing inventive compounds for producing electrically conductive and infrared-reflecting fluorine-doped tin oxide layers on glass, glass ceramic, and enamel surfaces.

These compounds, when dissolved in polar organic solvents, preferably lower aliphatic alcohols or ketones and without additional doping agents, minimize the surface resistance of tin oxide layers produced therewith on glass, glass ceramic and enamel surfaces and maximize the IR-reflection. The product is stable for a long time and, moreover, must be free of chlorine.

SUMMARY OF THE INVENTION

Surprisingly, these properties are to be found in new tin compounds, which correspond, pursuant to the invention, to the general formula $SnR^1_aR^2_bR^3_c$, in which
$R^1$ is an alkyl group with 1 to 4 carbon atoms,
$R^2$ is an acetate group,
$R^3$ is a trifluoroacetate group,
a has a value of 1 or 2,
b has a value of 1 or 2, and
c has a value of 1 or 2, with the proviso that the sum of $a+b+c=4$.

$R^1$ is an alkyl group with 1 to 4 carbon atoms and preferably a butyl group.

Examples of inventive compounds are $C_4H_9—Sn(CH_3COO)_2CF_3COO$, $(C_4H_9)_2—Sn(CH_3COO)CF_3COO$, $(C_3H_7)Sn(CH_3COO)_2CF_3COO$.

Compounds with only one alkyl group linked to Sn are preferred.

A further object of the invention is a method for synthesizing the inventive compounds, which is characterized in that acetic anhydride and trifluoroacetic anhydride are added in the well-known manner in the desired molar ratio with cooling to alkyl tin oxide in such a way, that a reaction temperature of 90° C. is not exceeded and, after the addition of the reactants, the reaction is completed at a temperature of about 80° to 90° C. during a period of 2 to 6 hours.

The invention furthermore relates to a material for producing electrically conductive and infrared-reflecting fluorine-doped tin oxide layers on glass, glass ceramic and/or enamel surfaces, with the distinguishing feature that said material contains tin compounds of the formula $SnR^1_aR^2_bR^3_c$ or mixtures of these tin compounds, the mixture corresponding to the general, average formula $SnR^1_xR^2_yR^3_z$, in which x has a numerical value of 1 to 2, y a numerical value of 0.1 to 2.9 and z a numerical value of 0.1 to 2.9, the sum of $x+y+z$ being 4, dissolved in a polar, organic solvent.

Preferably, the material contains mixtures of these tin compounds, in which x has a numerical value of 1, y a numerical value of 0.5 to 2.0 and z a numerical value of 0.5 to 2.0, the sum of $x+y+z$ being 4.

Pursuant to the invention, the concept of "mixtures" is to be understood in such a way that, corresponding to the molar ratios during the synthesis of the inventive compounds, the inventive material contains not only a single species of the new, inventive compounds, but a mixture of two or more of the inventive, new compounds. The subscripts x, y and z then indicate the average values of the alkyl, acetate and trifluoroacetate groups and can therefore assume fractional values.

The inventive compounds are dissolved in the inventive materials in polar, organic solvents. As polar, organic solvent, the inventive material contains an aliphatic alcohol with 1 to 4 carbon atoms or a ketone with 2 to 8 carbon atoms. Particularly preferred solvents are ethanol, isopropanol and acetone.

The inventive material preferably contains 40 to 60% by weight of the inventive tin compound(s) and 60 to 40% by weight of the organic solvent.

To form the desired, electrically conductive and infrared-reflecting layers, an inventive material is sprayed in a well-known manner by means of a spray gun using compressed air in a spraying-atomizing method onto the glass, glass ceramic or enamel surface, which has been heated to a temperature of 400° to 800° C. A fluorine-doped tin oxide layer is produced by pyrolysis on these surfaces. The thickness of this coating can vary between 100 nm and 2 $\mu$m. The layers, produced by the inventive method, are distinguished by a high transparency. The integral infrared reflection at wavelengths ranging from 2.5 to 15 $\mu$m is more than 80%.

The synthesis and application methods are described in greater detail in the following Examples, it being understood that these Examples are given by way of illustration and not by way of limitation.

EXAMPLE 1

Into a 1-liter, multi-neck flask, equipped with a KPG stirrer, 248.9 g of dibutyl tin oxide are weighed. While stirring slowly, 51.1 g of acetic anhydride and 105 g of trifluoroacetic anhydride ($x=2$, $y=1$, $z=1$) are added dropwise. The reaction is highly exothermic. Care has to be taken to ensure that the reaction temperature does not exceed 90° C. At the end of the addition, the temperature is maintained for a further 4 hours at 80° C. to 90° C. to complete the reaction.

The almost clear product, so obtained, is mixed with a little filter aid and activated charcoal and filtered through an AF 2000 filter plate by means of a filter press.

The clear product is sprayed as a 50% solution in ethanol onto a flat glass plate (160 mm×180 mm×6 mm), which had previously been heated for 5 minutes at a furnace temperature of about 700° C. The coated glass plate, when sprayed with 7 mL, has the following values:
 surface resistance: 11 ohms/square
 IR-reflection: 87%
 layer thickness: 750 nm

EXAMPLE 2

Into a 250 mL, multi-neck flask, provided with a KPG stirrer, 149.4 g of dibutyl tin oxide are weighed. While stirring slowly, 21.5 g of acetic anhydride and 84.0 g of trifluoroacetic anhydride ($x=2$, $y=1.3$, $z=0.7$) are added dropwise. The reaction is highly exothermic. Care has to be taken to ensure that the reaction temperature does not exceed 90° C. At the end of the addition, the temperature is maintained for a further 4 hours at 80° C. to 90° C. to complete the reaction.

The almost clear product, so obtained, is mixed with a little filter aid and activated charcoal and filtered through an AF 2000 filter plate by means of a filter press.

The clear product is sprayed as a 50% solution in ethanol onto a flat glass plate (160 mm×180 mm×6 mm), which had previously been heated for 5 minutes at a furnace temperature of about 700° C.

The coated glass plate, when sprayed with 7 mL, has the following values:
 surface resistance: 26 ohms/square
 IR-reflection: 75%
 layer thickness: 1130 nm

EXAMPLE 3

Into a 250 mL, multi-neck flask, provided with a KPG stirrer, 149.4 g of dibutyl tin oxide are weighed. While stirring slowly, 40.8 g of acetic anhydride and 42.0 g of trifluoroacetic anhydride ($x=2$, $y=0.7$, $z=1.3$) are added dropwise. The reaction is highly exothermic. Care has to be taken to ensure that the reaction temperature does not exceed 90° C. At the end of the addition, the temperature is maintained for a further 4 hours at 80° C. to 90° C. to complete the reaction.

The almost clear product, so obtained, is mixed with a little filter aid and activated charcoal and filtered through an AF 2000 filter plate by means of a filter press.

The clear product is sprayed as a 50% solution in ethanol onto a flat glass plate (160 mm×180 mm×6 mm), which had previously been heated for 5 minutes at a furnace temperature of about 700° C.

The coated glass plate, when sprayed with 10 mL, has the following values:
 surface resistance: 53 ohms/square
 IR-reflection: 60%
 layer thickness: 1100 nm

EXAMPLE 4

Into a 250 mL, multi-neck flask, provided with a KPG stirrer, 104.4 g of monobutyl tin oxide are weighed. While stirring slowly, 40.3 g of acetic anhydride and 78.8 g of trifluoroacetic anhydride ($x=1$, $y=1.5$, $z=1.5$) are added dropwise. The reaction is highly exothermic. Care has to be taken to ensure that the reaction temperature does not exceed 90° C. At the end of the addition, the temperature is maintained for a further 4 hours at 80° C. to 90° C. to complete the reaction.

The almost clear product, so obtained, is mixed with a little filter aid and activated charcoal and filtered through an AF 2000 filter plate by means of a filter press.

The clear product is sprayed as a 50% solution in ethanol onto a flat glass plate (160 mm×180 mm×6 mm), which had previously been heated for 5 minutes at a furnace temperature of about 700° C.

The coated glass plate, when sprayed with 7 mL, has the following values:
 surface resistance: 79 ohms/square
 IR-reflection: 51%
 layer thickness: 840 nm

EXAMPLE 5

Into a 250 mL, multi-neck flask, provided with a KPG stirrer, 104.4 g of monobutyl tin oxide are. weighed. While stirring slowly, 26.9 g of acetic anhydride and 105.0 g of trifluoroacetic anhydride ($x=1$, $y=1$, $z=2$) are added dropwise. The reaction is highly exothermic. Care has to be taken to ensure that the reaction temperature does not exceed 90° C. At the end of the addition, the temperature is maintained for a further 4 hours at 80° C. to 90° C. to complete the reaction.

The almost clear product, so obtained, is mixed with a little filter aid and activated charcoal and filtered through an AF 2000 filter plate by means of a filter press.

The clear product is sprayed as a 50% solution in isopropanol onto a flat glass plate (160 mm×180 mm×6 mm), which had previously been heated for 5 minutes at a furnace temperature of about 700° C.

The coated glass plate, when sprayed with 7 mL, has the following values:
 surface resistance: 75 ohms/square
 IR-reflection: 50%
 layer thickness: 840 nm

EXAMPLE 6

Into a 250 mL, multi-neck flask, provided with a KPG stirrer, 104.4 g of monobutyl tin oxide are weighed. While stirring slowly, 53.7 g of acetic anhydride and 52.5 g of trifluoroacetic anhydride ($x=1$, $y=2$, $z=1$) are added dropwise. The reaction is highly exothermic. Care has to be taken to ensure that the reaction temperature does not exceed 90° C. At the end of the addition, the temperature is maintained for a further 4 hours at 80° C. to 90° C. to complete the reaction.

The almost clear product, so obtained, is mixed with a little filter aid and activated charcoal and filtered through an AF 2000 filter plate by means of a filter press.

The clear product is sprayed as a 70% solution in acetone onto a flat glass plate (160 mm×180 mm×6 mm), which had previously been heated for 5 minutes at a furnace temperature of about 700° C.

The coated glass plate, when sprayed with 5 mL, has the following values:
 surface resistance: 87 ohms/square
 IR-reflection: 49%
 layer thickness: 1100 nm

What is claimed is:

1. A compound of the general formula $SnR^1_aR^2_bR^3_c$, wherein
   $R^1$ is an alkyl group with 1 to 4 carbon atoms,
   $R^2$ is an acetate group,
   $R^3$ is a trifluoroacetate group,
   a has a value of 1 or 2,
   b has a value of 1 or 2, and
   c has a value of 1 or 2, with the proviso that the sum of $a+b+c=4$.

2. A method for the synthesis of the compounds having the general formula $SnR^1_aR^2_bR^3_c$, wherein
   $R^1$ is an alkyl group with 1 to 4 carbon atoms,
   $R^2$ is an acetate group,
   $R^3$ is a trifluoroacetate group,
   a has a value of 1 or 2,
   b has a value of 1 or 2, and
   c has a value of 1 or 2, with the proviso that the sum of $a+b+c=4$,
   or their mixtures, comprising adding acetic anhydride and trifluoroacetic anhydride to alkyl tin oxide with cooling in such a way that a reaction temperature of 90° C. is not exceeded and, at the end of the addition of the reactants, carrying out the reaction at a temperature of about 80° to 90° C. during a period of 2 to 6 hours.

3. A material for preparing electrically conductive and infrared-reflecting fluorine-doped tin oxide layers on glass, glass ceramic, enamel, or all three surfaces, comprising tin compounds of the formula $SnR^1_aR^2_bR^3_c$, wherein
   $R^1$ is an alkyl group with 1 to 4 carbon atoms,
   $R^2$ is an acetate group,
   $R^3$ is a trifluoroacetate group,
   a has a value of 1 or 2,
   b has a value of 1 or 2, and
   c has a value of 1 or 2, with the proviso that the sum of $a+b+c=4$,
   or mixtures of these compounds, the mixture corresponding to the general formula $SnR^1_xR^2_yR^3_z$, wherein x has a numerical value of 1 to 2, y a numerical value of 0.1 to 2.9 and z a numerical value of 0.1 to 2.9, the sum of $x+y+z$ being 4, dissolved in a polar organic solvent.

4. The material of claim 3, comprising mixtures of tin compounds, in which x has a numerical value of 1, y a numerical value of 0.5 to 2.0 and z a numerical value of 0.5 to 2.0, the sum of $x+y+z$ being 4.

5. The material of claims 3 or 4, comprising, as polar organic solvent, an aliphatic alcohol with 1 to 4 carbon atoms or a ketone with 2 to 8 carbon atoms.

6. The material of claims 3 or 4, comprising 40% to 60% by weight of the tin compound or of the mixture of tin compounds, and 60% to 40% by weight of the organic solvent.

* * * * *